United States Patent
Burman et al.

(10) Patent No.: US 6,608,174 B1
(45) Date of Patent: Aug. 19, 2003

(54) RADIOLABELED VASOACTIVE INTESTINAL PEPTIDE ANALOGS FOR DIAGNOSIS AND RADIOTHERAPY

(75) Inventors: Anand C. Burman, Ghaziabad (IN); Sudhanand Prasad, Ghaziabad (IN); Rama Mukherjee, Ghaziabad (IN); Sarjana Dutt, Ghaziabad (IN); Rajan T. Sharma, Ghaziabad (IN); Rinku Ahuja, Ghaziabad (IN); Anil K. Mishra, Delhi (IN); Lazar T. Mathew, Delhi (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

(21) Appl. No.: 09/629,632

(22) Filed: Jul. 31, 2000

(30) Foreign Application Priority Data

Feb. 18, 2000 (IN) .................... 137/DEL/2000

(51) Int. Cl.$^7$ ............................. A61K 38/16
(52) U.S. Cl. .................. 530/324; 530/345; 514/2; 514/12; 424/1.11; 424/1.65; 424/1.69
(58) Field of Search ............... 530/324, 345; 514/2, 12; 424/1.11, 1.65, 1.69

(56) References Cited

U.S. PATENT DOCUMENTS

| | | | |
|---|---|---|---|
| 4,605,641 A | 8/1986 | Bolin et al. | 514/12 |
| 4,734,400 A | 3/1988 | Bolin et al. | 514/12 |
| 4,835,252 A | 5/1989 | Musso et al. | 530/324 |
| 4,866,039 A | 9/1989 | Wootton et al. | 514/16 |
| 5,141,924 A | 8/1992 | Bolin | 514/12 |
| 5,217,953 A | 6/1993 | Gozes et al. | 514/12 |
| 5,376,637 A | 12/1994 | Sawai et al. | 514/12 |
| 5,428,015 A | 6/1995 | Kurono et al. | 514/12 |
| 5,565,424 A | 10/1996 | Gozes et al. | 514/12 |
| 5,677,419 A | 10/1997 | Bolin et al. | 530/317 |
| 5,849,261 A | 12/1998 | Dean et al. | 424/1.69 |
| 6,007,792 A | 12/1999 | Dean et al. | 424/1.69 |

FOREIGN PATENT DOCUMENTS

| | | |
|---|---|---|
| EP | 0796867 | 9/1997 |
| WO | 9101144 | 7/1991 |
| WO | 9630055 | 10/1996 |
| WO | 0005260 | 3/2000 |

OTHER PUBLICATIONS

Kiyoshi Nokihara, et al.; Receptrecognition of Pacap and VIP . . . Substitution; Peptides 1996; Robert Ramage et al.; (Eds. 1998 The European Peptide Society; p. 63–66.

H. Frucht et al.; Characterization of Functional Receptors for Gastrointestinal Hormones on Human Colon Cancer Cells; Cancer Research 52; 1114–1122; Mar. 1, 1992.

Irene Virgolini et al.; Vasoactive Intestinal Peptide–Receptor Imagine for the Localization of Intestinal . . . Tumors; New England Journal of Medicine; vol. 331 (17); 1116–1121; Oct. 27, 1994.

G.Lilling et al.; Inhibition of Human Neuroblastoma Growth by a Specific VIP Antagonist; Journal of Molecular Neuroscience; vol. 5, 1994/1995; 231–239.

Gozes et al.; Vasoactive Intestinal Peptide Potentiates Sexual Behavior; Inhibition by Novel Antagonist Endocrinology; vol. 125, No. 6; 2945–2949; (1989).

Primary Examiner—Christopher S. F. Low
Assistant Examiner—David Lukton
(74) Attorney, Agent, or Firm—Ladas & Parry

(57) ABSTRACT

The present invention encompasses radiolabeled peptide analogs of vasoactive intestinal peptide (VIP) labeled with a radionuclide useful for imaging target sites within mammalian living systems. The invention particularly provides radiolabeled VIP derivatives that bind selectively to the VIP receptor on target cells. Specifically, the invention relates to the radiolabeling of VIP-receptor specific agents and their subsequent use for radiodiagnostic and radiotherapeutic purposes. The invention encompasses methods for radiolabeling these peptides with radio-nuclides and the use of these peptides as scintigraphic imaging agents. The radiolabeled VIP derivatives of the present invention exhibit pharmacological activity and therefore are useful as either imaging agent for visualization of VIP-receptor positive tumors and metastases, as a radiodiagnostic agent or as a radio-therapeutic agent for the treatment of such tumors in vivo by specifically targeting the cytotoxic radionuclide selectively to the tumor site in mammalian living systems.

38 Claims, 1 Drawing Sheet

Radioimage of a mammalian tumour xenografted nude mice using the radiolabelled VIP analog.
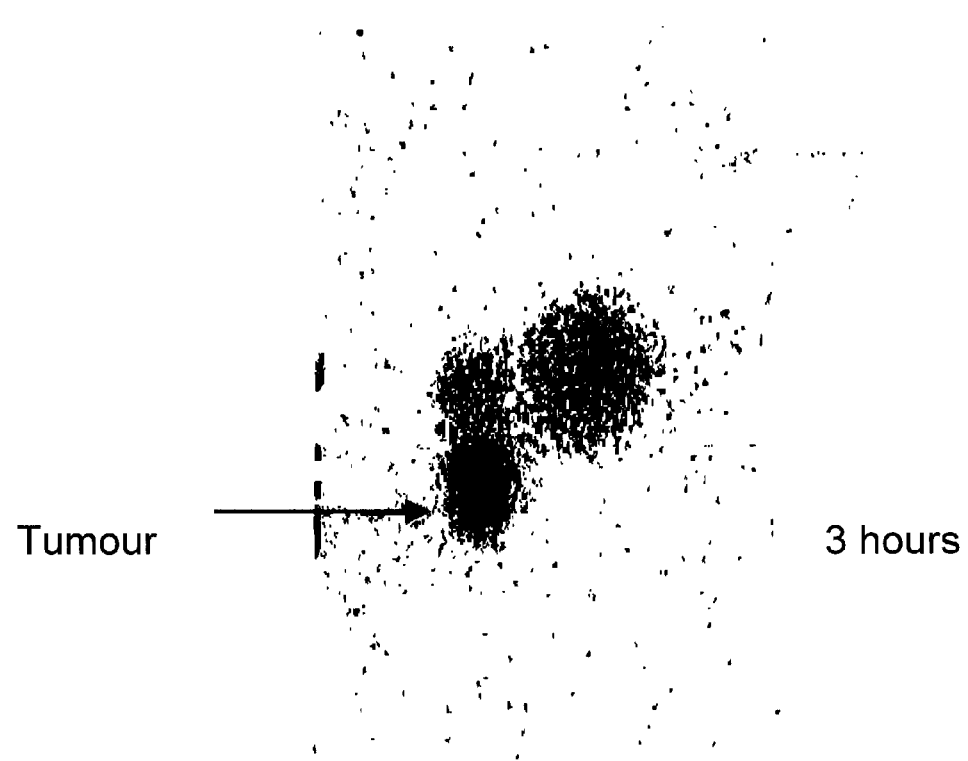
Tumour
3 hours
F I G. 1

RADIOLABELED VASOACTIVE INTESTINAL PEPTIDE ANALOGS FOR DIAGNOSIS AND RADIOTHERAPY

FIELD OF THE INVENTION

The present invention encompasses radiolabeled peptide analogs of vasoactive intestinal peptide (VIP) labeled with a radionuclide useful for imaging target sites within mammalian living systems. The invention particularly provides radiolabeled VIP derivatives that bind selectively to the VIP receptor on target cells. Specifically, the invention relates to the radiolabeling of VIP-receptor specific agents and their subsequent use for radiodiagnostic and radiotherapeutic purposes. The invention encompasses methods for radiolabeling these peptides with radionuclides and the use of these peptides as scintigraphic imaging agents. The radiolabeled VIP derivatives of the present invention exhibit pharmacological activity and therefore are useful as either imaging agent for visualization of VIP-receptor positive tumors and metastases, as a radiodiagnostic agent or as a radiotherapeutic agent for the treatment of such tumors in vivo by specifically targeting the cytotoxic radionuclide selectively to the tumor site in mammalian living systems.

BACKGROUND OF THE INVENTION

Vasoactive intestinal peptide is a 28-amino acid neuropeptide, which was first isolated from the porcine intestine (Said and Mutt, 1970). It bears extensive homology to secretin, PHI and glucagon. The amino acid sequence for VIP is:

His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH$_2$ (SEQ ID NO: 1)

VIP is known to exhibit a wide variety of biological activities such as the autocrine, endocrine and paracrine functions in living organisms (Said, 1984). In the gastrointestinal tract, it has been known to stimulate pancreatic and biliary secretions, hepatic glycogenesis as well as the secretion of insulin and glucagon (Kerrins and Said, 1972; Domschke et al., 1977). In the nervous system it acts as a neurotransmitter and neuromodulator, regulating the release and secretion of several key hormones (Said, 1984). In recent years, attention has been focussed on the function of VIP in certain areas of the CNS as well its role in the progression and control of neoplastic disease (Reubi, 1995).

The importance of peptide growth factors and regulatory hormones in the etiology and pathogenesis in several carcinomas has long been recognized. Data from epidemiological and endocrinological studies suggest that neuropeptides like VIP which are responsible for the normal growth of tissues like the pancreas can also cause conditions for their neoplastic transformation (Sporn et al., 1980). Several lines of evidence indicate that VIP acts as a growth factor and plays a dominant autocrine and paracrine role in the sustained proliferation of cancer cells (Said, 1984). The stimulatory effect of VIP on tumor growth can be mediated directly by its receptors on cell membranes or indirectly by potentiation of the activities of other growth factors in tumor cells (Scholar E. M. Cancer 67(6): 1561–1569, 1991). The synergistic effect of VIP and related pituitary adenylate cyclase activating polypeptide (PACAP) in glioblastomas is an illustration to the above fact (Moody, T. W., et al. Peptides 17(3), 545–555, 1996).

The multiple physiological and pharmacological activities of VIP are mediated by high affinity G-protein coupled transmembrane receptors on target cells (Reubi, 1995). VIP receptors are coupled to cellular effector systems via adenylyl cyclase activity (Xia et al., 1996). The VIP receptor, found to be highly over-expressed in neoplastic cells, is thought to be one of the biomarkers in human cancers (Reubi, 1995). High affinity VIP receptors have been localized and characterized in neoplastic cells of most breast carcinomas, breast and prostate cancer metastases, ovarian, colonic and pancreatic adenocarcinomas, endometrial and squamous cell carcinomas, non small cell lung cancer, lymphomas, glioblastomas, astrocytomas, meningiomas and tumors of mesenchymal origin. Amongst, neuroendocrine tumors all differentiated and non-diffemtiated gastroenteropancreatic tumors, pheochromocytomas, small-cell lung cancers, neuroblastomas, pituitary adenomas as well tumors associated with hypersecretory states like Verner-Morrison syndrome were found to overexpress receptors for vasoactive intestinal peptide (Reubi, 1995, 1996, 1999; Tang et al., 1997a&b; Moody et al., 1998a&b; Waschek et al., 1995; Oka et al., 1998)). These findings suggest that new approaches for the diagnosis and treatment of these cancers may be based on functional manipulation of VIP activity, using synthetic peptide analogs of the same.

Historically, the somatostatin analog $^{111}$In-DTPA-[D-Phe$^1$]-octreotide is the only radiopeptide, which has obtained regulatory approval in USA and Europe (Lamberts et al., 1995). Radiolabeled VIP has been shown to visualize a majority of gastropancreatic adenocarcinomas, neuroendocrine tumors, as well as insulinomas (which are often missed by radiolabeled octreotide) (Behr et al., 1999). VIP-receptor scinitigraphy offers certain advantages over radioimaging involving somatostatin receptors. The presence of high affinity receptors for VIP have been demonstrated in a larger number of human tumors, relative to the somatostatin receptors. Secondly, the density of VIP receptors on tumors has been found to be greater than somatostatin (Behr et al., 1999). Therefore, the VIP-receptor scan is more sensitive and convenient in localizing tumors and their metastatic spread as compared to somatostatin. The applications of this technique are manifold. It has been used for the sensitive detection of VIP-receptor positive tumors. This includes primary carcinoids, cancers of the gastrointestinal tract as well as distant metastases (Reubi, 1995, 1996). It can also be used to target cytotoxic radionuclides specifically to the tumor site. It predicts the VIP-receptor status of the patient and thereby the response of the patient towards radiotherapy by radiolabeled VIP analogs. Lastly, such radiolabeled peptides have been successfully used in radioguided surgery (Lamberts et al., 1995).

$^{123}$I-VIP, $^{125}$I-VIP and their derivatives have been extensively used for imaging pancreatic adenocarcinomas, endocrine tumors of the gastrointestinal origin, mesenchymal tumors as well secondary tumor metastatic sites, in patients (Jiang et al., 1997; Virgolini et al., 1996, 1998; Raderer et al., 1998 ; Moody et al., 1998; Kurtaran et al., 1997; Pallella et al., 1999). Radioiodinated VIP and its derivatives have been also used to assess the binding affnty of peptides for VIP-receptors on tumor cells in vitro. The biodistribution, safety and absorbed dose of the aforesaid radioiodinated peptide derivatives have also been studied earlier (Virgolini et al., 1995).

U.S. Pat. No. 5,849,261, granted to Dean et al., on Dec. 15, 1998 describes the applications of radiolabeled vasoactive intestinal peptide (VIP) for diagnosis and therapy. In particular, this U.S. Patent discloses a method for preparing a radiopharmaceutical agent, comprising native vasoactive intestinal (VIP) peptide attached to a radionuclide like technetium or rhenium via a chelating moiety. The radiopharmaceutical when labeled with technetium or rhenium via a chelating moiety has a VIP binding affinity which is not less than about one tenth the affinity of radioiodinated native VIP for the receptor.

However, there is still a need for improved synthetic analogs of VIP as radiopharmaceuticals, which are easy to generate and are capable of being employed with higher sensitivity and specificity in terms of their radioimaging and radiodiagnostic properties.

This invention describes the preparation and use of peptide analogs of VIP having constrained amino acids. The design of conformationally constrained bioactive peptide derivatives has been one of the widely used approaches for the development of peptide-based therapeutic agents. Non-standard amino acids with strong conformational preferences may be used to direct the course of polypeptide chain folding, by imposing local stereochemical constraints, in de novo approaches to peptide design. The conformational characteristics of α,α-dialkylated amino acids have been well studied. The incorporation of these amino acids restricts the rotation of φ, Ψ angles, within the molecule, thereby stabilizing a desired peptide conformation.

The prototypic member of α,α-dialkylated aminoacids, α-amino-isobutyric acid (Aib) or α,α-dimethylglycine has been shown to induce β-turn or helical conformation when incorporated in a peptide sequence (Prasad and Balaram, 1984, Karle and Balaram, 1990). The conformational properties of the higher homologs of α,α-dialkylated amino acids such as di-ethylglycine (Deg), di-n-propylglycine (Dpg), di-n-butylglycine (Dbg) as well as the cyclic side chain analogs of α,α-dialkylated amino acids such as 1-aminocyclopentane carboxylic acid (Ac5c), 1-aminocyclohexane carboxylic acid (Ac6c), 1-aminocycloheptane carboxylic acid (Ac7c) and 1-aminocyclooctane carboxylic acid (Ac8c) have also been shown to induce folded conformation (Prasad et al., 1995 ; Karle et al., 1995). α,α-dialkylated amino acids have been used in the design of highly potent chemotactic peptide analogs (Prasad et al., 1996). The present invention incorporates the conformational properties of such α,α-dialkylated amino acids for the design of biologically active peptide derivatives, taking VIP as the model system under consideration.

REFERENCES

Behr T. M. et al. Q. J. Nucl. Med., 43, 268–280,1999.
Domschke, S. et al. Gastroenterology, 73, 478–480, 1977.
Jiang S. et al. Cancer Res., 57, 1475–1480,1997.
Karle, L L. et al. (1995) J. Amen Chem. Soc. 117, 9632–9637.
Karle, L L. and Balaram, P. (1990) Biochemistry 29, 6747–6756.
Kerrins, C. and Said, S. I. Proc. Soc. Exp. Biol. Med., 142, 1014–1017, 1972.
Kurtaran A. et al. J. Nucl. Med., 38, 880–881, 1997.
Lamberts, S. W. J. et al. In Somatostatin and its Receptors, Ciba Found. Symp., 190, 222–239, 1995.
Moody, T. W. et al. Peptides, 19 (3), 1998a.
Moody, T. W. et al. Ann. N.Y. Acad. Sci., 865, 290–296. 1998b.
Oka, H. et al. Am. J. Pathol., 153 (6), 1787–1796, 1998.
Pallella, V. R. et al. J. Nucl. Med., 40(2), 352–360, 1999.
Prasad, B. V. V and Balaram, P. (1984) CRC Crit. Rev. Biochem. 16, 307–347.
Prasad, S et al. (1995) Biopolymers 35, 11–20.
Prasad, S et al. (1996) Int. J. Peptide Protein Res. 48, 312–318.
Reubi, J. C. J. Nucl. Med., 36 (10), 1995.
Reubi, J. C. et al. Int. J. Cancer, 81 (3), 1999.
Reubi, J. C. et al. Cancer Res., 56 (8), 1922–1931, 1996.
Raderer, M. et al. J. Nucl. Med., 39 (9), 1570–1575, 1998.
Said, S. I. and Mutt, V. Science, 169, 1217–1218,1970.
Said, S. I. Peptides, 5, 143–150, 1984.
Sporn, M. B., and Todaro, G. J. N. Engl. J. Med., 303, 378–379, 1980.
Tang, C. et al., Gut, 40 (2), 267–271, 1997a.
Tang, C. et al., Br. J. Cancer, 75 (10)1467–1473, 1997b.
Virgolini, I. et al. J. Nucl. Med., 36(10), 1732–1739, 1995.
Virgolini, I. et al. Nucl. Med. Biol., 23 (6), 685–692, 1996.
Virgolini, I. et al. J. Nucl. Med., 39 (9), 1998.
Waschek, J. A. et al. Cancer Lett., 92 (2), 1995.
Xia, M. et al., J. Clin. Immunol., 16 (1), 21–30, 1996.

Throughout the specification and claims the following abbreviations are used:
Aib: α-Aminoisobutyric acid
Deg: α,α-Diethylglycine
Ac5c: 1-Amino Cyclopentane Carboxylic acid
BOP: Benzotriazole-1-yl-oxy-tris-(dimethylamino)-phosphonium hexofluorophosphate
PyBOP: Benzotriazole-1-yl-oxy-tris-pyrrolidino-phosphonium hexofluorophospate
HBTU: O-Benzotriazole-N,N,N',N'-tetramethyl-uronium-hexofluoro-phosphate
TBTU: 2-(1H-Benzotriazole-1-yl)-1, 1, 3, 3-tetramethyluronium tetrafluoroborate
HOBt: 1-Hydroxy Benzotriazole
DCC: Dicyclohexyl carbodiimide
DIPCDI: Diisopropyl carbodiimide
DIEA: Diisopropyl ethylamine
DMF: Dimethyl formamide
DCM: Dichloromethane
NMP: N-Methyl-2-pyrrolidinone
TFA: trifluoroacetic acid Throughout the specification and claims the amino acid residues are designated by their standard abbreviations. Amino acids denote L-configuration unless indicated by D or DL appearing before the symbol and separated from it by a hypen.

SUMMARY OF THE INVENTION

The present invention encompasses radiolabeled peptide analogs of vasoactive intestinal peptide (VIP) labeled with a radionuclide useful for imaging target sites (e.g. use as a scintigraphic imaging agent), for use in radiodiagnostics, and radiotherapy within mammalian living systems. The invention particularly provides radio labeled VIP derivatives that bind selectively to the VIP receptor on target cells. Specifically, the invention relates to the radiolabeling of VIP receptor specific agents and their subsequent use for radiodiagnostic and radiotherapeutic purposes. The invention encompasses methods for radiolabeling these peptides with radionuclides and the use of these peptides as scintigraphic imaging agents. The present invention also encompasses the use of these radiolabeled peptides as anti-neoplastic agents for specific radiotherapy in cancer. A further object of the invention is the use of certain novel VIP analogs to determine the binding affinities of these peptides for their cognate receptors on cancer cells.

BRIEF DESCRIPTION OF THE FIGURE

FIG. 1 shows a radioimage of a mammalian tumor xenografted nude mouse using a radiolabeled VIP analog.

DETAILED DESCRIPTION OF THE INVENTION

The present invention provides novel radiolabeled peptide analogs of vasoactive intestinal peptide useful for imaging target sites within a mamalian living system, comprising a synthetic receptor-binding peptide analog of vasoactive intestinal peptide (VIP) radiolabeled with a radionuclide. The present invention relates to the use of the radiolabeled peptides, processes for production of the radiolabeled peptides, pharmaceutical preparations for its use as a diagnostic, imaging as well as a radiotherapeutic agent in vivo.

The VIP peptide analogs of the present invention, which is a VIP receptor antagonist has the sequence:

His-Ser-Asp-Xxx-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ where Xxx is Aib, Deg or Ac5c or a pharmaceutically acceptable salt of the peptide.

A preferred peptide is:
His-Ser-Asp-Aib-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO: 2)

or a pharmaceutically acceptable salt thereof.

Salts encompassed within the term "pharmaceutically acceptable salts" refer to non-toxic salts of the compounds of this invention. Representative salts and esters include:

acetate, ascorbate, benzenesulfonate, benzoate, bicarbonate, bisulfate, bitartrate, borate, camsylate, carbonate, citrate, dihydrochloride, methanesulfonate, ethanesulfonate, p-toluenesulfonate, cyclohexylsulfamate, quinate, edetate, edisylate, estolate, esylate, fumaxate, gluconate, glutamate, glycerophophates, hydrobromide, 5 hydrochloride, hydroxynaphthoate, lactate, lactobionate, laurate, malate, maleate, mandelate, mesylate, mucate, napsylate, nitrate, n-methylglucamine, oleate, oxalate, palmoates, pamoate (embonate), palmitate, pantothenate, perchlorates, phosphate/diphosphate, polygalacturonate, salicylates, stearate, succinates, sulfate, sulfamate, subacetate, succinate, tannate, tartrate, tosylate, trifluoroacetate and valerate.

Other salts include Ca, Li, Mg, Na and K salts; salts of amino acids such lysine or arginine; guanidine, diethanolamine or choline; ammonium, substituted ammonium salts or aluminum salts. The salts can be prepared by standard techniques.

The VIP receptor antagonist:
His-Ser-Asp-Xxx-Val4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ where Xxx is Aib, Deg or Ac5c have been shown in co-pending application Ser. No. 09/630,335 (filed on Jul. 31, 2000) to be selectively binding to VIP receptors on cancer cells. The anti-proliferative activity of the aforesaid VIP antagonist has been previously demonstrated in a number of experimental models of pancreatic, prostate, mammary and lung cancer, suggesting its high anti-neoplastic therapeutic potential.

The applicants have found that the VIP analogs of the present invention have greater affinity for its cognate receptors on tumor cells as compared to native VIP, which in turn leads to better radio-imaging, radiodiagnostic and radiotherapeutic efficacy of the radiopharmaceuticals of the present invention. While not wishing to be bound by theory, the applicants believe that the improved efficacy of the radiopharmaceuticals of the present invention are due to the nature of the VIP analogs themselves, which have receptor bound conformations caused by the incorporation of the unusual amino acids.

The labeling of peptides by a radionuclide has been accomplished in the present invention, by several strategies:

1. Direct labeling of radionuclide to the peptide analogs.
2. attachment of chelating groups to the peptide and subsequent radiolabeling by radionuclide.
3. Incorporation of radionuclide to chelator moieties covalently linked to the peptide via a spacer group.

It is important to note that in the above cases, the chelator and spacer groups are incorporated site-specifically at a position which does not affect the specific binding properties of the peptide to the VIP receptor on tumor cells in vitro and in vivo.

In a preferred embodiment of the present invention, the radionuclide is selected from Technetium (Tc-99m), Iodine 123 ($^{123}$I), Iodine 131 ($^{131}$I), Indium-111 ($^{111}$I) and Rhenium-188 ($^{188}$Re).

One embodiment of the invention involves the radiolabeling of the VIP antagonists directly by a radionuclide such as Tc-99m. Tc-99m forms a coordinate covalent linkage with certain specific amino acid residues of the peptide. The formation of a stable Tc-peptide bond is one of the major advantages for its use for imaging purposes. The attachment of Tc-99m to the peptide involves the reaction of a salt of Tc-99m such as pertechnate to the peptide, in the presence of a reducing agent such as dithionate ion, ferrous ion or stannous chloride. The radiolabeled peptides are separated from the unincorporated Tc-99m as described in the examples and used for radioscintography.

Another embodiment of the present invention includes the attachment of certain chelating groups to the VIP analog. The chelating groups are capable of complexing a detectable element such as a radionuclide. According to the invention, the chelating moiety may be attached directly or indirectly to the peptide, e.g. by means of a spacer or a bridging group to the amino terminus of the VIP analog. In a more preferred embodiment of the invention the radionuclide is Tc-99m bound to a chelating moiety. All the radiolabeled chelated peptides retain their affinity for VIP receptors on cancer cells.

According to one embodiment of the invention, the chelating group has substantial hydrophobic character. Examples of chelating groups include e.g. iminodicarboxylic groups, polyarninopolycarboxylic groups, e.g. those derived from non-cyclic ligands e.g. ethylene diamine tetra acetic acid (EDTA), diethylene triamine pentaacetic acid (DTPA), ethylene glycol-0,0'-bis (2-aminoethyl) N,N,N',N'-tetraacetic acid (EGTA), N,N'-bis(hydroxybenzyl) ethylenediamine-N,N'-diacetic acid (HBED) and triethylen-etrianinehexaacetic acid (TTHA).

The chelating groups derived from macrocyclic ligands include, e.g. 1,4,7,10-tetra-azacyclododecane-N,N',N",N'"-tetra acetic acid (DOTA), 1,4,7,10-tetra-azacyclotridecane-1,4,7,10-tetra acetic acid (TITRA), 1,4,8,11 -tetra-azacyclotetradecane-N,N',N",N'"-tetra acetic acid (TETA), 1,4,8,11 -tetra-azacyclotetradecane (TETRA) and aryl chelating moieties e.g. hydrazinonicotinamide (HYNIC).

While conventional chelating agents are within the scope of the present invention, the applicants have, for the first time, employed certain novel MAG3 derivatives as chelating agents. The present invention also encompasses chelating groups based on peptides e.g. preferred derivatives of mercaptoacetyltriglycine (MAG3) which are not previously known to be employed as chelating agents in this field.

MAG 3 chelating agents include:
SH—CH$_2$—CO-Gly-Gly-Gly
Cys-Gly-Aib-Ala (SEQ ID NO: 3)

Cys-Gly-Gly-Aib (SEQ ID NO:4)
Gly-Gly-Ala-Aib (SEQ ID NO: 5)
Cys-Aib-Gly-Gly (SEQ ID NO: 6)
Cys-Ala-Gly-Aib (SEQ ID NO: 7)
Gly-Gly-Gly-Aib (SEQ ID NO: 8)
Gly-Gly-Aib-Ala (SEQ ID NO: 9)

These MAG3 peptide derivatives are preferredchelating groups.

When the MAG3 peptide derivatives are used a spacer group is required. The preferred spacer groups are amino acids of the formula $NH_2—(CH_2)_n—COOH$ where n is 4, 5 or 6. When n is 4 the spacer group is 5-amino pentanoic acid. When n is 5 the spacer group is 6-amino hexanoic acid or amino caproic acid. When n is 6 the spacer group is 5-amino heptanoic acid. When a spacer is used, the VIP analog is attached to the carboxylic end of the spacer and the chelating moiety to the amino end.

In a preferred embodiment the novel peptide reagent comprises 33 amino acids: 28 from a VIP analog, 1 from a spacer group and 4 from a chelating moiety attached to radiolabeled nuclide to provide a novel and hitherto unknown radiotherapeutic and radioscintographic agent.

The methods involved in the synthesis, purification, characterization and radiolabeling of these peptides are illustrated in detail in the examples. The following section also includes biological data relating to the imaging efficacy and dosimetry of the aforesaid radiolabeled peptides. The examples have been furnished for illustrating and providing insight into the invention and should not be construed as limiting the scope of the invention.

EXAMPLES

Solid Phase Pelptide Synthesis

An analog of the present invention can be made by exclusively solid phase techniques, by partial solid phase/ solution phase techniques and/or by fragment condensation.

Methods for chemical synthesis of polypeptides are well known in the art. Stewart and Young, Solid Phase Peptide Synthesis (W. H. Freeman and Co., 1969), Atherton and Shepherd, 1988, J. Chem. Soc. Perkin Trans. I, 2287. Preferred, semi automated, stepwise solid phase methods for synthesis of peptides of the invention are provided in the examples below.

Example 1

Preparation of VIP Analogs

Peptides were synthesized using preferably, Fmoc (9-fluorenyl methoxy carbonyl) solid-phase methodology, on CS Bio (Model 536) Peptide Synthesizer (CS Bio Co., San Carlos, Calif., U.S.A.).

Sequential assembly of a peptide analog was conducted from the carboxy terminus, by loading of a Fmoc protected amino acid to a solid-phase resin, to the amino terminus. This was proceeded by subsequent removal of the Fmoc protecting group of the amino acid and a stepwise, sequential addition of Fmoc protected amino acids in repetitive cycles to obtain an intermediate protected peptide resin.

For peptides that were amidated at the carboxy-terminus, Rink Amide resin was employed, and the loading of the first Fmoc protected amino acid was affected via an amide bond formation with the solid support, mediated by diisopropyl-carbodiimide and HOBt. Substitution levels for automated synthesis were preferably between 0.2 and 0.8 mmole amino acid per gram resin.

Steps in the synthesis of VIP analogs encompassed in the present invention, employed the following protocol:

| STEP | REAGENT | MIX TIME (MIN) | NO. OF TIMES |
|---|---|---|---|
| 1. | Methylene chloride | 1 | 2 |
| 2. | Dimethyl formamide | 1 | 1 |
| 3. | 20% Piperidine in Dimethyl formamide | 1 | 1 |
| 4. | 20% Piperidine in Dimethyl formamide | 29 | 1 |
| 5. | Dimethyl formamide | 1 | 3 |
| 6. | Isopropanol | 1 | 2 |
| 7. | Methylene chloride | 1 | 2 |
| 8. | Amino Acid | Variable | 1 |
| 9. | Dimethyl formamide | 1 | 2 |
| 10. | Stop or Return for next cycle | | |

The 9-fluorenyl methoxy carbonyl (Fmoc) group was used for the protection of the α-amino group of all amino acids employed in the syntheses. However, other protecting groups known in the art for α-amino group may be employed successfully. Side chain functional groups were protected as follows: Trityl (trt) and t-butyloxycarbonyl (Boc) were the preferred protecting groups for the imidazole group of Histidine. ydroxyl groups of serine, threonine and tyrosine were protected by t-butyl (t-Bu) groups. mc (2,2, 5,7,8-pentamethyl-chroman-6-sulfonyl) and Pbf (2,2,4,6,7-pentamethyldihydro benzofuiran-5-sulfonyl) were the preferred protecting groups for the guanido group in Arginine. Trityl protection was used for asparagine and glutamine. Tryptophan was either used with Boc protection or unprotected. The lysine side chain was Boc protected and aspartic acid and glutamic acid had t-butyl side chain protection.

The resin employed for the synthesis of carboxy-amidated analogs was 4-(2',4'Dimethoxyphenyl-Fmoc-aminomethyl)-phenoxymethyl-derivatized polystyrene 1% divinylbenzene (Rink Amide) resin (100–200 mesh), procured from Calbioichem-Novabiochem Corp., La Jolla, U.S.A., (0.47 milliequivalent $NH_2$/g resin).

Typically, 2–8 equivalents of Fmoc protected amino acid per resin nitrogen equivalent were used. The activating reagents used for coupling of amino acids in the solid phase synthesis of peptides are well known in the art. These include DCC, DIPCDI, DIEA, BOP, PyBOP, HBTU, TBTU, and HOBt. Preferably, DCC or DIPCDI/HOBt or HBTU/HOBT and DIEA couplings were carried out.

Swelling of the resin was typically carried out in dichloromethane measuring to volumes 10–40 ml/g resin. The protected amino acids were either activated in situ or r added in the form of preactivated esters known in the art such as NHS esters, Opfp esters etc. Atherton, E. et al. 1988, J. Chem. Soc. Perkin Trans. I. 2887, Bodansky, M. in "Peptides, Analysis, Synthesis and Biology (E. Gross, J. Meienhofer eds.) Vol. I, Academic Press, New York, 1979, 106.

Coupling reaction was carried out in DMF, DCM or NMP or a mixture of these solvents and was monitored by Kaiser test (Kaiser et al., Anal. Biochem., 34, 595–598, 1970). Any incomplete reactions were re-coupled using freshly prepared activated amino acids.

After complete assembly of the analog, the amino-terminal Fmoc group was removed using steps 1–6 of the above protocol and then the peptide-resin was washed with methanol and dried. The analogs were then deprotected and cleaved from the resin support by treatment with trifluoroacetic acid, crystalline phenol, ethanedithiol, thioanisole and de-ionized water for 1.5 to 5 hours at room temperature. The crude peptide was obtained by precipitation with cold dry ether, filtered, dissolved and lyophilized.

The resulting crude peptide was purified by preperative high performance liquid chromatography (HPLC) using a LiChroCART® C18 (250. Times. 10) reverse phase column (Merck, Darmstadt, Germany) on a Preparative HPLC system (Shimadzu Corporation, Japan) using a gradient of 0.1% TFA in acetonitrile and water.

The eluted fractions were reanalyzed on Analytical HPLC system (Shimadzu Corporation, Japan) using a C,8 LiChrospher®, WP-300 (300.Times.4) reverse-phase column. Acetonitrile was evaporated and the fractions were lyophilized to obtain the pure peptide. The identity of each peptide was confirmed by electron spray mass spectroscopy.

(a) Preparation of Fmoc-Asn(trt)-Resin

A typical preparation of the Fmoc-Asn(trt)-resin was earned out using 0.5 g of 4-(2',4'-Dimethoxyphenyl-Fmoc-aminomethyl) phenoxymethyl-derivatized polystyrene 1% divinylbenzene (Rink Amide) resin (0.47 mM/g) (100–200 mesh), procured from Calbiochem-Novabiochem Corp., La Jolla, U.S.A. The resin was first allowed to swell in methylene chloride (2. Times. 25ml for 10 min.). It was washed once in dimethylformamide for 1 min. All solvents in the automated protocol were in 20 ml portions per addition. The Fmoc-protecting group on the resin was removed by following steps 3 to 7 of the synthesis protocol. Deprotection of the Fmoc group was checked by the presence of blue beads in a positive Kaiser test. For loading of the first amino acid on the free amino ($NH_2$) group of the resin, the first amino acid, Fmoc-Asn(trt)-OH, was weighed in four fold excess, along with a similar fold excess of HOBt, in the amino acid vessel of the peptide synthesizer. These were dissolved in dimethylformamide (A.C.S. grade) (J. T. Baker, Phillipsburg, N.J., U.S.A.) and activated with DIPCDI, just prior to the addition to the resin in the reaction vessel of the peptide synthesizer. HOBt was added in all coupling reactions, especially in the case of Arg, Asn, Gin and His. The coupling reaction was carried out for a period ranging from 1–3 hours. Loading of the first amino acid was complete when Kaiser test gave a negative result and there was adequate weight increase when the resin, with the first amino acid attached, was dried in vacuum overnight and weighed.

Example 2

(b) Synthesis of His-Ser-AsM-Aib-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-$NH_2$ (SEQ ID NO: 2)

The synthesis of SEQ ID NO:2 was initiated by using all of the resin loaded with FmocAsn(trt)-OH as prepared in example (a) above. This was subjected to stepwise deprotection and coupling steps as in steps 1–10 of the synthesis cycle. In each coupling reaction, a four-fold excess of amino-acid, DIPCDI and HOBt were used.

The amounts of components are summarized in the table below:

| CYCLE | GRAMS OF PROTECTED AMINO ACID |
|---|---|
| 1. | 0.333 Leu |
| 2. | 0.333 Ile |
| 3. | 0.361 Ser |
| 4. | 0.560 Asn |
| 5. | 0.333 Leu |

-continued

| CYCLE | GRAMS OF PROTECTED AMINO ACID |
|---|---|
| 6. | 0.432 Tyr |
| 7. | 0.441 Lys |
| 8. | 0.441 Lys |
| 9. | 0.319 Val |
| 10. | 0.292 Ala |
| 11. | 0.333 Leu |
| 12. | 0.575 Gln |
| 13. | 0.441 Lys |
| 14. | 0.625 Arg |
| 15. | 0.333 Leu |
| 16. | 0.625 Arg |
| 17. | 0.374 Thr |
| 18. | 0.432 Tyr |
| 19. | 0.560 Asn |
| 20. | 0.387 Asp |
| 21. | 0.374 Thr |
| 22. | 0.396 4-Cl-D-Phe |
| 23. | 0.319 Val |
| 24. | 0.292 Ala |
| 25. | 0.387 Asp |
| 26. | 0.361 Ser |
| 27. | 0.449 His |

Upon completion of synthesis and removal of the N-terminal Fmoc protecting group (steps 1–6 of the synthesis cycle), the peptide-resin was washed twice with methanol, dried and weighed to obtain 0.560 g. This was subjected to cleavage in a cleavage mixture consisting of trifluoroacetic acid and scavengers, crystalline phenol, ethanedithiol, thioanisole and water for a period of 1.5–5 hours at room temperature with continuous stirring. The peptide was precipitated using cold dry ether to obtain ~280 mg of crude peptide. The crude peptide was purified on a $C_{18}$ preparative reverse phase HPLC column (250. Times. 10) on a gradient of acetonitrile and water in 0.1% TFA as described elsewhere. The prominent peaks were collected and lyophilized, reanalysed on analytical HPLC and subjected to mass analysis. The calculated mass was ~3356.16 and the mass obtained was 3357.2. The HPLC pure peptide was then subjected to bio-analysis.

Incorporation of Spacer/bridging and Chelating Groups to Peptide Derivatives

Example 3

Synthesis of DTPA-Spacer-VIP Analog DTPA-Acp-His-Ser-Asp-Aib-Val-4-Cl-D-Phe-Thr-AsD-Asn-Tyr-Thr-Arg-Leu-Arg-Lys-Gln-Leu-Ala-Val-Lys-Lys-Tyl-Leu-Asn-Ser-Ile-Leu-Asn-$NH_2$ (SEQ ID NO: 10)

The attachment of the spacer groups to the peptide derivatives was carried out on solid phase. 0.5 gm of peptide-resin of consisting of peptide sequence (b) (SEQ ID NO:2) was synthesized in the same way as described in Example 2. The N-teminal end was deprotected using piperidine. The spacer Amino caproic acid (Acp) was converted to Fmoc-Acp following the standard method of N-terminal protection of amino acid. Fmoc-Acp (185mg) was dissolved in DMF and coupled to the peptide resin using DIPCDI/HOBt as the coupling agent. The completion of the reaction was monitored by standard Kaiser test. It was further deprotected and coupled to DTPA anhydride in presence of DIPCDI/HOBt. After completion of the reaction it was dried. 530 mg of peptide containing spacer and chelate on resin was obtained and was cleaved as described in Example 2. 282 mg crude peptide-conjugate was obtained which was further purified by HPLC and characterized.

Example 4

Synthesis of MAG3 Derivative-Spacer-VIP Analog
Cys-Gly-Aib-Ala-Acp-His-Ser-Asp-Aib-Val-4-Cl-D-
Phe-Thr-Asp-Asn-Tyr-Thr-Arg-Leu-Arg-Lys-Gln-
Leu-Ala-Val-Lys-Lys-Tyr-Leu-Asn-Ser-Ile-Leu-Asn-
NH$_2$ (SEQ ID NO: 11)

The spacer group Acp was attached to VIP analog in the same way on solid phase as described in Example 3. 1.3 gm of peptide resin on which VIP analog and spacer group i.e. Acp are assembled was taken and the four amino acids Ala, Aib, Gly and Cys were coupled respectively following the same protocol as described in Example 2. 1.398 of peptide-resin were obtained on cleavage which yielded 675.0 mg of crude peptide conjugate. It was further purified and characterized.

General Methods for Radiolabeling

In forming a complex of radioactive technetium with a peptide of this invention (SEQ ID NO:2) the technetium complex, preferably a salt of Tc-99m pertechnetate, was reacted with a peptide of this invention in the presence of a reducing agent such as stannous ion, dithionite ion or ferrous ion. In a preferred embodiment, the reducing agent is stannous ion.

Example 5

1 mg of the peptide of SEQ ID NO:2 was dissolved in 1 ml of water or 0.9% normal saline. To 100 μg of freshly dissolved peptide 8–15 μg of stannous chloride dissolved in 10% acetic acid was added. pH is set to 5.5 with 0.5N NaHCO$_3$, 1–10 mCi of freshly eluted Tc-99m sodium pertechnetate is added to the peptide, the reaction proceeds at room temperature for 15–45 minutes and then is filtered through a 0.22 μm filter.

The radiolabeled peptide was either used directly or purified on a Sep Pak C18 cartridge using 50% MeCN-water/0.1% TFA as eluant. The extent of Tc-99m peptide labeling achieved was determined by instant thin layer chromatography (ITLC). 5 μl of the radiopharmaceutical was spotted at the base of silica gel coated ITLC strips and chromatographed with acetone or normal saline. Under these conditions 99% of Tc99m associated radioactivity remained at the origin (Rf=0) in either solvent indicating that no significant concentration of free Tc-99m pertechnetate could be detected in the sample.

Example 6

Alternatively, the peptide of SEQ ID NO:2 was reacted with technetium-99m in a reduced form.

Example 7

In another alternative, both SEQ ID NO:2 and technetium-99m were reacted with a reducing agent prior to being reacted with each other; preferred reducing agent being stannous ion (other reducing agents include dithionite and ferrous ions).

Example 8

In forming a complex of radioactive technetium with the MAG3 chelated peptide (SEQ ID NO:1 1), the technetium complex, preferably a salt of Tc-99m pertechnetate, was reacted with a peptide of this invention in the presence of a reducing agent; in a preferred embodiment, the reducing agent is stannous ion (other reducing agents include dithionite and ferrous ions). 1 mg of the MAG3-peptide was dissolved in 1 ml of water or 0.9% normal saline. To 100 υg of freshly dissolved peptide 8–15 υg of stannous chloride dissolved in 10% acetic acid was added. pH was set to 5.5 with 0.5N NaHCO$_3$. 1–10 mCi of freshly eluted Tc-99m sodium pertechnetate was added to the peptide, the reaction proceeded at room temperature for 15–45 minutes and then filtered through a 0.22 μm filter.

The radiolabeled peptide was either used directly or purified on a Sep Pak C18 cartridge using 50%MeCN-water/0.1% TFA as eluant. The extent of Tc-99m peptide labeling achieved was determined by instant thin layer chromatography (ITLC). 5 μl of the radiopharmaceutical was spotted at the base of silica gel coated ITLC strips and chromatographed with acetone or normal saline. Under these conditions 99% of Tc99m associated radioactivity remained at the origin (Rf=0) in either solvent indicating that no significant concentration of free Tc-99m pertechnetate could be detected in the sample.

Example 9

Alternatively, the MAG3-peptide complex was reacted with technetium-99m in a reduced form.

Example 10

In another alternative, both the MAG3-peptide complex and technetium-99m were reacted with a reducing agent prior to being reacted with each other; preferred reducing agent being stannous ion (other reducing agents include dithionite and ferrous ions).

Example 11

In forming a complex of radioactive technetium with the DTPA chelated peptide (SEQ ID NO:10), the technetium complex, preferably a salt of Tc-99m pertechnetate, was reacted with the peptide of this invention in the presence of a reducing agent; in a preferred embodiment, the reducing agent being stannous ion (other reducing agents include dithionite and ferrous ions). 1 mg of the DTPA-peptide was dissolved in 1 ml of water or 0.9% normal saline. 100 υg of freshly dissolved peptide added 8–15 μg of stannous chloride dissolved in 10% acetic acid was added. pH was set to 5.5 with 0.5N NaHCO$_3$. 1–10 mCi of freshly eluted Tc-99m sodium pertechnetate was added to the peptide, the reaction proceeded at room temperature for 15–45 minutes and then filtered through a 0.22 μm filter.

The radiolabeled peptide was either used directly or purified on a Sep Pak C18 cartridge using 50%MeCN-water/0.1% TFA as eluant. The extent of Tc-99m peptide labeling achieved was determined by instant thin layer chromatography (ITLC). 5 μl of the radiopharmaceutical was spotted at the base of silica gel coated ITLC strips and chromatographed with acetone or normal saline. Under these conditions 99% of Tc-99m associated radioactivity remained at the origin (Rf=0) in either solvent indicating that no significant concentration of free Tc-99m pertechnetate could be detected in the sample.

Example 12

Alternatively, the DTPA-peptide complex of the invention was reacted with technetium-99m in a reduced form.

Example 13

In another alternative, both the DTPA-peptide complex of the invention and technetium-99m were reacted with a reducing agent prior to being reacted with each other; preferred reducing agent being stannous ion (other reducing agents include dithionite and ferrous ions).

Example 14

Other radionuclides that may be used to radiolabel the peptides—the VIP receptor antagonists are those known in the art and include $^{123}$I, $^{131}$I, $^{111}$In, and $^{188}$Re etc.

In vitro Biological Assays

Example 15

Peptides of the invention were assayed for biological activity in homogeneous competition binding assays using $^{125}$I labeled VIP peptide (SEQ ID NO:1) and in heterogeneous displacement assays using either $^{125}$I labeled VIP (10–28) fragment (Tyr-Thr-Arg-Leu-Arg-Lys-Gln-Met-Ala-Val-Lys-Lys-Tyr-Leu-Asn-Ser-Ile-Leu-Asn-NH$_2$) (SEQ ID NO: 12) or $^{125}$I labeled VIP (SEQ ID NO:1). The assays were performed on a variety of human tumor cell lines.

In the practice of these methods, the peptide was radio-iodinated using the iodogen method. Briefly, 5 μg of the peptide in 10 μl of 50 mM PBS (pH 7.5), an appropriate amount of the radioisotope and 50 μg–100 μg iodogen were incubated at room temperature for 15–30 min with occasional mixing. Radioiodinated peptide was purified from unincorporated radioactive iodine by purification on a Sep Pak C$_{18}$ cartridge, essentially following the same procedure as described for technetium labeling.

Example 16

Receptor binding and competition assays were performed at 4–8° C. Briefly, 50,000 cells were plated per well of a 24 well plate and allowed to adhere overnight. Before the assay, the cells were washed twice with ice cold binding buffer (25 mM HEPES, 10 mM MgCl$_2$ and 1% BSA in RPMI 1640 medium). The cells were incubated for 2–3 hrs with an appropriate concentration (0.1–10 nM) of the $^{125}$I labeled peptide (SEQ ID NO:2), in the presence and absence of the cold ligand, which is the uniodinated form of the same peptide (1 nM–10 μM). After incubation, the cells were washed thrice with the binding buffer to remove the unbound peptide. The cells were lysed and counts were measured in a Gamma counter. From a comparison of the extent of binding in the presence or absence of the unlabeled peptide (SEQ ID NO:2), the dissociation constant (Kd) (TABLE I) and maximal binding (Bmax) (TABLE II) were calculated for the peptide. It was observed that the peptide bound to two kinds of receptors on the cell surface. One receptor had a high affinity (nM range) but low surface expression on the cells whereas the other receptor had a low affinity (υM range) but high expression on the cell surface. These characteristics are similar to what has been previously reported for VIP receptors.

The following tumor cell lines were assayed using the above described binding competition assay: HT29 (human colorectal adenocarcinoma); PTC (human primary tumor cells adenocarcinoma); KB (human squamous cell carcinoma); 4451 (human squamous cell carcinoma); L132 (human lung carcinoma); A549 (human lung carcinoma); HBL100 (human breast carcinoma) and PA1 (human ovarian carcinoma). Cells were grown in RPMI 1640 supplemented with 10% fetal calf serum, glutamine and antibiotics using standard cell culture techniques (see Animal Cell Culture: A Practical Approach, Freshney, ed, IRL press: Oxford, UK, 1992).

TABLE I

| S No. | CELL LINES | K$_{d1}$ (nM) | K$_{d2}$ (μM) |
|---|---|---|---|
| 1) | PTC | 1.77 | 1.18 |
| 2) | HT29 | 3.8 | 1.37 |
| 3) | KB | 4.2 | 1.84 |
| 4) | 4451 | 4.48 | 1.91 |
| 5) | L132 | 2.6 | 1.03 |
| 6) | A549 | 2.09 | 1.53 |
| 7) | HBL 100 | 2.13 | 1.6 |
| 8) | PA1 | 5.6 | 1.89 |

TABLE II

| SNo. | CELL LINES | Bmax$_1$ (M) | Bmax$_2$ (M) |
|---|---|---|---|
| 1) | PTC | 8.3E-10 | 9.66E-08 |
| 2) | HT29 | 3.67E-10 | 6.72E-08 |
| 3) | KB | 6.02E-10 | 4.29E-08 |
| 4) | 4451 | 5.79E-10 | 5.1E-08 |
| 5) | L132 | 3.06E-10 | 4.58E-08 |
| 6) | A549 | 5.40E-10 | 4.83E-08 |
| 7) | HBL 100 | 6.97E-10 | 6.91E-08 |
| 8) | PAI | 5.29E-10 | 4.77E-08 |

Example 17

Displacement assays were performed at 4–8° C. Briefly, 50,000 cells were plated per well of a 24 well plate and allowed to adhere overnight. Before the assay, the cells were washed twice with ice cold Binding buffer (25 mM HEPES, 10 mM MgCl$_2$ and 1% BSA in RPMI 1640 medium). The cells were incubated for 2–3hrs with an appropriate concentration (0.1–10 nM) of $^{125}$I labeled VIP (10–28) fragment (SEQ ID NO:12) in the presence and absence of the cold ligand (SEQ ID NO: 2) (1 nM–10 μM). The non specific binding was ascertained using 10 μM of VIP. After incubation, the cells were washed thrice with the binding buffer to remove the unbound peptide. The cells were lysed and counts were measured in a Gamma counter. From a comparison of the extent of binding in the presence or absence of the unlabeled peptide, a concentration was determined corresponding to inhibition of $^{125}$I labeled VIP (10–28) fragment binding by 50% (termed the IC$_{50}$) (TABLE III).

The following tumor cell lines were assayed using the above described displacement assay: HT29 (human colorectal adenocarcinoma); PTC (human primary tumor cells adenocarcinoma); KB (human squamous cell carcinoma); 4451 (human squamous cell carcinoma); L132 (human lung carcinoma); A549 (human lung carcinoma); HBL100 (human breast carcinoma) and PA1 (human ovarian carcinoma).

Cells were grown in RPMI 1640 supplemented with 10% fetal calf serum, glutamine and antibiotics using standard cell culture techniques (see Animal Cell Culture: A Practical Approach, Freshney, ed, IRL press: Oxford, UK, 1992).

TABLE III

| S No. | CELL LINES | IC$_{50}$ (pM) |
|---|---|---|
| 1) | PTC | 132 |
| 2) | HT29 | 220 |
| 3) | KB | 350 |
| 4) | 4451 | 383 |
| 5) | L132 | 228 |

TABLE III-continued

| S No. | CELL LINES | IC$_{50}$ (pM) |
|---|---|---|
| 6) | A549 | 275 |
| 7) | HBL 100 | 236 |
| 8) | PA1 | 310 |

Example 18

Displacement assays were performed at 4–8° C. Briefly, 50,000 cells were plated per well of a 24 well plate and allowed to adhere overnight. Before the assay, the cells were washed twice with ice cold Binding buffer (25 mM HEPES, 10 mM 15 MgCl$_2$ and 1% BSA in RPMI 1640 medium). The cells were incubated for 2–3hrs with an appropriate concentration (0.1–10 nM) of $^{125}$I labeled VIP (SEQ ID NO:1) in the presence and absence of the cold ligand (SEQ ID NO: 2) (1 nM–10 μM). The non specific binding was ascertained using 10 μM of VIP. After incubation, the cells were washed thrice with the Binding buffer to remove the unbound peptide. The cells were lysed and counts were measured in a Gamma counter. From a comparison of the extent of binding in the presence or absence of the unlabeled peptide, a concentration was determined corresponding to inhibition of $^{125}$I labeled VIP binding by 50%. Different tumor cell lines were assayed using the above described displacement assay: HT29 (human colorectal adenocarcinoma); PTC (human primary tumor cells adenocarcinoma); KB (human squamous cell carcinoma); 4451 (human squamous cell carcinoma); L132 (human lung carcinoma); A549 (human lung carcinoma); HBL100 (human breast carcinoma) and PA1 (human ovarian carcinoma). Cells were grown in RPMI 1640 supplemented with 10% fetal calf serum, glutamine and antibiotics using standard cell culture techniques (see Animal Cell Culture: A Practical Approach, Freshney, ed, IRL press: Oxford, UK, 1992). The ligand i.e. VIP analog was able to significantly displace the binding of radiolabelled VIP to the cell lines as shown in Table IV.

TABLE IV

| S No. | CELL LINES | IC$_{50}$ (nM) |
|---|---|---|
| 1) | PTC | 2.53 |
| 2) | HT29 | 2.78 |
| 3) | KB | 6.2 |
| 4) | 4451 | 7.1 |
| 5) | L132 | 6.8 |
| 6) | A549 | 4.3 |
| 7) | HBL 100 | 5.41 |
| 8) | PA1 | 7.6 |

These results demonstrate that the VIP analog described in the invention is capable of specifically binding to VIP receptors in standard in vitro assays on a variety of human tumor cell types.

Imaging of Human Tumor Induced in Nude Mice

Example 19

Tc-99m labeled peptide (SEQ ID NO: 10) was used to image tumors induced subcutaneously in the abdomen of NIH nu/nu nude mice. Following intravenous administration in human adenocarcinoma tumor bearing nude mice, images were taken at different time intervals post infection, using a conventional gamma camera. A rapid blood clearance was observed with little accumulation in liver and kidney while tumor uptake was found to achieve significant levels as early as 15 min post injection. The major pathway of clearance for the labeled peptide of the invention is through the kidneys as shown by a significant activity in the bladder and urine. These results indicate that the VIP analogue of the present invention (SEQ ID NO:2) has utility as scintigraphic imaging agent for imaging tumor of adenocarcinoma origin in humans. Maximum binding was seen at 3 hours leading to greater accumulation of radioactivity in tumors in comparison to the normal visceral tissue. The results are shown in FIG. 1 which clearly depicts that the accumulation of Tc-99m labeled VIP analog is high in tumor (indicated with arrow) as compared to the accumulation in viscera (unmarked dots) after 3 hours of injection.

All publications referenced are incorporated by reference herein including the amino acid sequences listed in each publication. All the compounds disclosed and referred to in the publications mentioned above are incorporated by reference herein, including those compounds disclosed and referred to in the articles cited by the publications.

What is claimed is:

1. A radiolabeled peptide analog of vasoactive intestinal peptide comprising a receptor-binding peptide analog of vasoactive intestinal peptide (VIP) radiolabeled with a radionuclide wherein said receptor-binding peptide analog of vasoactive intestinal peptide is of the sequence:

His-Ser-Asp-Xxx-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:13)

where Xxx is Aib (α-amino isobutyric acid), Deg (α,α-diethylglycine) or Ac5c (1-aminocyclopentane carboxylic acid) or a salt thereof.

2. The peptide analog of claim 1, wherein the radionuclide is Tc99m, $^{111}$In, $^{123}$I, 131I, or $^{188}$Re.

3. A method of detecting the presence of vasoactive intestinal peptide (VIP) receptor-bearing cells in a mammal comprising:

(a) administering to said mammal a radiolabeled peptide analog of VIP according to claim 2 for a time and under conditions effective to achieve binding between the radiolabeled peptide analog and said VIP receptor-bearing cells, and (b) determining the distribution of the radiolabeled peptide analog for a time and under conditions effective to obtain a scintigraphic image of said mammal.

4. A method of detecting the presence of vasoactive intestinal peptide (VIP) receptor-bearing cells in a mammal comprising:

(a) administering to said mammal a radiolabeled peptide analog of VIP according to claim 1 for a time and under conditions effective to achieve binding between the radiolabeled peptide analog and said VIP receptor-bearing cells, and (b) determining the distribution of the radiolabeled peptide analog for a time and under conditions effective to obtain a scintigraphic image of said mammal.

5. A radiolabeled peptide analog of vasoactive intestinal peptide comprising a receptor-binding peptide analog of vasoactive intestinal peptide (VIP) radiolabeled with a radionuclide, and a chelating moiety wherein said receptor-binding peptide analog of vasoactive intestinal peptide is of the sequence:

His-Ser-Asp-Xxx-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:13)

wherein Xxx is Aib (α-amino isobutyric acid), Deg (α,α-di-ethylglycine) or Ac5c (1-aminocyclopentane carboxylic acid) or a salt thereof.

6. The radiolabeled peptide analog as claimed in claim 5, wherein the chelating group is selected from the group consisting of ethylene diamine tetraacetic acid (EDTA), diethylene triamine pentaacetic acid (DTPA), ethyleneglycol-0,0'-bis(2-aminoethyl)-N,N,N',N'-tetraacetic acid (EGTA), N,N'-bis (hydroxybenzyl) ethylene diamine-N,N'-diacetic acid (HBED) and triethylenetriamine hexacetic acid (TTHA).

7. The peptide analog of claim 6, wherein the radionuclide is Tc99m, $^{111}$In, $^{123}$I, $^{131}$I, or $^{188}$Re.

8. A method of detecting the presence of vasoactive intestinal peptide (VIP) receptor-bearing cells in a mammal comprising:

(a) administering to said mammal a radiolabeled peptide analog of VIP according to claim 6 for a time and under conditions effective to achieve binding between the radiolabeled peptide analog and said VIP receptor-bearing cells, and (b) determining the distribution of the radiolabeled peptide analog for a time and under conditions effective to obtain a scintigraphic image of said mammal.

9. The radiolabeled peptide analog as claimed in claim 5, wherein the chelating group is selected from the group consisting of 1,4,7,10-tetra-azacyclododecan-N,N',N',N'-tetraacetic acid (DOTA), 1,4,7,1 0-tetra-azacyclotridecane-1,4,7,10 tetra acetic acid (TITRA), 1,4,8,11-tetra-azacyclotetradecane-N,N',N'',N'''-tetraacetic acid (TETA), 1,4,8,11-tetra-azacyclotetradecane (TETRA) and hydrazinonicotinamide (HYNIC).

10. The radiolabeled peptide-analog as claimed in claim 5, wherein the chelating moiety is a mercaptoacetyltriglycine 3 (MAG3) chelating group.

11. The peptide analog of claim 5, wherein the radionuclide is Tc99m, $^{111}$In, $^{123}$I, $^{131}$I, or $^{188}$Re.

12. The radiolabeled peptide analog as claimed in claim 10, wherein the MAG3 chelating group is selected from:

SH—CH$_2$—CO-Gly-Gly-Gly, Cys-Gly-Aib-Ala (SEQ ID NO: 3), Cys-Gly-Gly-Aib (SEQ ID NO: 4), Gly-Gly-Ala-Aib (SEQ ID NO: 5), CysAib-Gly-Gly (SEQ ID NO: 6), Cys-Ala-Gly-Aib (SEQ ID NO: 7), Gly-Gly-Gly-Aib (SEQ ID NO: 8) or Gly-Gly-Aib-Ala (SEQ ID NO: 9).

13. The peptide analog of claim 12, wherein the radionuclide is Tc99m, $^{111}$In, $^{123}$I, $^{131}$I, or $^{188}$Re.

14. A method of detecting the presence of vasoactive intestinal peptide (VIP) receptor-bearing cells in a mammal comprising:

(a) administering to said mammal a radiolabeled peptide analog of VIP according to claim 5 for a time and under conditions effective to achieve binding between the radiolabeled peptide analog and said VIP receptor-bearing cells, and (b) determining the distribution of the radiolabeled peptide analog for a time and under conditions effective to obtain a scintigraphic image of said mammal.

15. A method of detecting the presence of vasoactive intestinal peptide (VIP) receptor-bearing cells in a mammal comprising:

(a) administering to said mammal a radiolabeled peptide analog of VIP according to claim 12 for a time and under conditions effective to achieve binding between the radiolabeled peptide analog and said VIP receptor-bearing cells, and (b) determining the distribution of the radiolabeled peptide analog for a time and under conditions effective to obtain a scintigraphic image of said mammal.

16. A radiolabeled peptide analog of vasoactive intestinal peptide comprising a receptor-binding peptide analog of vasoactive intestinal peptide (VIP) radiolabeled with a radionuclide, a chelating moiety and a HN—(CH$_2$)$_n$—CO wherein said peptide analog of vasoactive intestinal peptide is of the sequence:

His-Ser-Asp-Xxx-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:13)

wherein Xxx is Aib (α-amino isobutyric acid), Deg (α,α-di-ethylglycine) or Ac5c (1-aminocyclopentane carboxylic acid) or salt thereof.

17. A method of detecting the presence of vasoactive intestinal peptide (VIP) receptor-bearing cells in a mammal comprising:

(a) administering to said mammal a radiolabeled peptide analog of VIP according to claim 16 for a time and under conditions effective to achieve binding between the radiolabeled peptide analog and said VIP receptor-bearing cells, and (b) determining the distribution of the radiolabeled peptide analog for a time and under conditions effective to obtain a scintigraphic image of said mammal.

18. The peptide analog of claim 16, wherein the radionuclide is Tc99m, $^{111}$In, $^{123}$I, $^{131}$I, or $^{188}$Re.

19. A radiolabeled peptide analog of vasoactive intestinal peptide comprising a synthetic receptor-binding peptide analog of vasoactive intestinal peptide (VIP) radiolabeled with Tc-99m and a chelating moiety, wherein said receptor-binding peptide analog of vasoactive intestinal peptide is of the sequence:

His-Ser-Asp-Xxx-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:13)

wherein Xxx is Aib (α-amino isobutyric acid), Deg (α,α-di-ethylglycine) or Ac5c (1-aminocyclopentane carboxylic acid) or salt thereof and said chelating moiety is selected from the group consisting of:

SH—CH$_2$—CO-Gly-Gly-Gly, Cys-Gly-Aib-Ala (SEQ ID NO:3), Cys-Gly-Gly-Aib (SEQ ID NO:4), Gly-Gly-Ala-Aib (SEQ ID NO:5), Cys-Aib-Gly Gly (SEQ ID NO:6), Cys-Ala-Gly-Aib (SEQ ID NO:7), Gly-Gly-Gly-Aib (SEQ ID NO:8) and Gly-Gly-Aib-Ala (SEQ ID NO:9).

20. A method of detecting the presence of vasoactive intestinal peptide (VIP) receptor-bearing cells in a mammal comprising:

(a) administering to said mammal a radiolabeled peptide analog of VIP according to claim 19 for a time and under conditions effective to achieve binding between the radiolabeled peptide analog and said VIP receptor-bearing cells, and (b) determining the distribution of the radiolabeled peptide analog for a time and under conditions effective to obtain a scintigraphic image of said mammal.

21. A radiolabeled vasoactive peptide analog vasoactive intestinal peptide comprising a synthetic receptor-binding peptide analog of vasoactive intestinal peptide (VIP) radiolabeled with Tc-99m, a chelating moiety, wherein said receptor-binding peptide analog of vasoactive intestinal peptide is of the sequence:

His-Ser-Asp-Xxx-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:13)

wherein Xxx is Aib (α-amino isobutyric acid), Deg (α,α-di-ethylglycine) or Ac5c (1-aminocyclopentane carboxylic acid) or a salt thereof and HN—(CH$_2$)$_n$—CO wherein n is 4, 5 or 6 and the chelating moiety is selected from the group consisting of:

SH—CH$_2$—CO-Gly-Gly-Gly, Cys-Gly-Aib-Ala (SEQ ID NO:3), Cys-Gly-Gly-Aib (SEQ ID NO:4), Gly-Gly-Ala-Aib (SEQ ID NO:5), Cys-Aib-Gly Gly (SEQ ID NO:6), Cys-Ala-Gly-Aib (SEQ ID NO:7), Gly-Gly-Gly-Aib (SEQ ID NO-8) and Gly-Gly-Aib-Ala (SEQ ID NO:9).

22. The radiolabeled vasoactive peptide analog as claimed in claim 21, comprising 33 amino acids of which 28 are from the peptide, one is from the spacer and four are from the chelating group.

23. A radiolabled peptide analog of vasoactive intestinal peptide comprising a synthetic receptor-binding peptide analog of vasoactive intestinal peptide (VIP) radiolabeled with Tc-99m, a chelating moiety and a spacer group, wherein said receptor-binding peptide analog of vasoactive intestinal peptide is of the sequence:

His-Ser-Asp-Xxx-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:13)

wherein Xxx is Aib (α-amino isobutyric acid), Deg (α,α-di-ethylglycine) or Ac5c (1-aminocyclopentane carboxylic acid) and said chelating moiety is diethylene triamine pentaacetic acid and the spacer group is of the formula HN—(CH$_2$)$_n$—CO where n is 4, 5 or 6.

24. A method of detecting the presence of vasoactive intestinal peptide (VIP) receptor-bearing cells in a mammal comprising:

(a) administering to said mammal a radiolabeled peptide analog of VIP according to claim 23 for a time and under conditions effective to achieve binding between the radiolabeled peptide analog and said VIP receptor-bearing cells, and (b) determining the distribution of the radiolabeled peptide analog for a time and under conditions effective to obtain a scintigraphic image of said mammal.

25. A method for producing a mixture that contains a radiolabeled vasoactive peptide for use in mammalian systems which comprises reacting a salt of a radionuclide with an analog of vasoactive intestinal peptide having the sequence, His-Ser-Asp-Xxx-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:13)

where Xxx is Aib (α-amino isobutyric acid), Deg (α,α-di-ethylglycine) or Ac5c (1-aminocyclopentane carboxylic acid) in the presence of a reducing agent for a time and under conditions effective to produce the radiolabeled peptide analog.

26. The method of claim 25, wherein the radionuclide is Tc99m, $^{111}$In, $^{123}$I, 131I or $^{188}$Re.

27. A method for producing a mixture that contains a radiolabeled vasoactive peptide analog which comprises coupling a chelating group to an analog of vasoactive intestinal peptide having the sequence, His-Ser-Asp-Xxx-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:13)

wherein Xxx is Aib (α-amino isobutyric acid), Deg (α,α-di-ethylglycine) or Ac5c (1-aminocyclopentane carboxylic acid), and reacting the analog with a radionuclide in the presence of a reducing agent for a time and under conditions effective to produce the radiolabeled peptide analog.

28. The method as claimed in claim 27, wherein the chelating group is selected from the group consisting of ethylenediaminetetraacetic acid (EDTA), diethylene triaminepentaacetic acid (DTPA), ethyleneglycol-0,0'-bis(2-aminoethyl)-N,N,N',N'-tetraacetic acid (EGTA), N,N',bis(hydroxybenzyl)ethylenediamine-N,N'-diacetic acid (HBED) and triethylenetriaminehexaacetic acid (TTHA).

29. The method as claimed in claim 27, wherein the chelating group is selected from the group consisting of 1,4,7,10-tetra-azacyclododecane-N,N',N'',N'''-tetraacetic acid (DOTA), 1,4,7,10-tetra-azacyclotridecane-1,4,7,10-tetraacetic acid (TITRA), 1,4,8,11-tetra-azacyclotetradecane-N,N',N'',N'''-tetraacetic acid (TETA), 1,4,8,11-tetra-azacyclotetradecane (TETRA) and hydazinonicotinamide (HYNIC).

30. The method as claimed in claim 27, wherein said chelating group is selected from the group consisting of mercaptoacetyltriglycine (MAG3), SH—CH$_2$—CO-Gly-Gly, Cys-Gly-Aib-Ala (SEQ ID NO:3), Cys-Gly-Gly-Aib (SEQ ID NO:4), Gly-Gly-Ala-Aib (SEQ ID NO:5), Cys-Aib-Gly-Gly (SEQ ID NO:6), Cys-Ala-Gly-Aib (SEQ ID NO:7), Gly-Gly-Gly-Aib (SEQ ID NO:8) and Gly-Gly-Aib-Ala (SEQ ID NO:9).

31. The method of claim 27, wherein the radionuclide is Tc99m, $^{111}$In, $^{123}$I, $^{131}$I, or $^{188}$Re.

32. A method for producing a mixture that contains radiolabelled vasoactive peptide analog which comprises coupling a spacer group of the formula

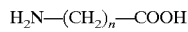

$H_2N-(CH_2)_n-COOH$ to an analog of vasoactive intestinal peptide having the sequence His-Ser-Asp-Xxx-Val-4-Cl-D-Phe-Thr-Asp-Asn-Tyr-Thr-Arg-Leu-Arg-Lys-Gln-Leu-Ala-Lys-Lys-Tyr-Leu-Asn-Ser-Ile-Leu-Asn-NH$_2$ (SEQ ID NO: 13)

wherein n is 4, 5 or 6,

Xxx is Aib (α-amino isobutyric acid), Deg (α, α-diethylglycine) or Ac5c (1-aminocyclopentane carboxylic acid), coupling a chelating group to the spacer group and reacting the analog with a radionuclide in the presence of a reducing agent for a time and under conditions effective to produce the radiolabelled peptide analog.

33. A method for producing a mixture that contains radiolabeled vasoactive peptide analog which comprises coupling a spacer group to an analog of vasoactive intestinal peptide having the sequence, His-Ser-Asp-Xxx-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:13)

wherein Xxx is Aib (α-amino isobutyric acid), Deg (α,α-di-ethylglycine) or Ac5c (1-aminocyclopentane carboxylic acid), coupling a chelating group to the spacer group and reacting the analog with a radionuclide in the presence of a reducing agent for a time and under conditions effective to produce the radiolabeled peptide analog.

34. The method as claimed in claim 33, wherein the chelating group is selected from the group consisting of ethylenediaminetetraacetic acid (EDTA), diethylene triaminepentaacetic acid (DTPA), ethyleneglycol-0,0'-bis(2-aminoethyl)N,N,N',N'-tetraacetic acid (EGTA), N,N',bis(hydroxybenzyl)ethylenediamine-N,N'-diacetic acid (HBED) and triethylenetriaminehexaacetic acid (TTHA).

35. The method as claimed in claim 33, claim wherein the chelating group is selected from the group consisting of 1,4,7,10-tetra-azacyclododecane-N,N',N",N'"-tetraacetic acid (DOTA), 1,4,7,10-tetra-azacyclotridecane-1,4,7,10-tetraadetic acid (TITRA), 1,4,8,11-tetra-azacyclotetradecane-N,N',N",N'"-tetraacetic acid (TETA), 1,4,8,11-tetra azacyclo-tetradecane (TETRA) and hydrazinonicotinamide (HYNIC).

36. The method as claimed in claim 33, wherein said chelating group is selected from the group consisting of mercaptoacetyltriglycine (MAG3), SH—$CH_2$—CO-Gly-Gly-Gly, Cys-Gly-Aib-Ala (SEQ ID NO:3), Cys-Gly-Gly-Aib (SEQ ID NO:4), Gly-Gly-Ala-Aib (SEQ ID NO:5), Cys-Aib-Gly-Gly (SEQ ID NO:6), Cys-Ala-Gly-Aib (SEQ ID NO:7), Gly-Gly-Gly-Aib (SEQ ID NO:8) and Gly-Gly-Aib-Ala (SEQ ID NO:9).

37. The method as claimed in claim 33, wherein the spacer is of the formula HN—$(CH_2)_n$—CO.

38. The method of claim 33, wherein the radionuclide is Tc99m, $^{111}$In, $^{123}$I, $^{131}$I, or $^{188}$Re.

* * * * *

SEQUENCE LISTING

<160> NUMBER OF SEQ ID NOS: 12

<210> SEQ ID NO 1
<211> LENGTH: 28
<212> TYPE: PRT
<213> ORGANISM: Sus barbatus

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

```
<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (4)
<223> OTHER INFORMATION: /product = alpha-aminoisobutyric/label = Aib
<221> NAME/KEY: MOD_RES
<222> LOCATION: (6)
<223> OTHER INFORMATION: /product = 4-chloro-D-phenylalanine/label =
      4-Cl-D-Phe

<400> SEQUENCE: 2

His Ser Asp Xaa Val Xaa Thr Asp Asn Tyr Thr Arg Leu Arg Lys Gln
 1               5                  10                  15

Leu Ala Val Lys Lys Tyr Leu Asn Ser Ile Leu Asn
            20                  25

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (3)
<223> OTHER INFORMATION: /product = alpha-aminoisobutryic/label = Aib

<400> SEQUENCE: 3

Cys Gly Xaa Ala
 1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (4)
<223> OTHER INFORMATION: /product = alpha-aminoisobutryic/label = Aib

<400> SEQUENCE: 4

Cys Gly Gly Xaa
 1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (4)
<223> OTHER INFORMATION: /product = alpha-aminoisobutryic/label = Aib

<400> SEQUENCE: 5

Gly Gly Ala Xaa
 1

<210> SEQ ID NO 6
<211> LENGTH: 4
<212> TYPE: PRT
<213> ORGANISM: Artificial Sequence
```

```
<220> FEATURE:
<223> OTHER INFORMATION: Description of Artificial Sequence: This
      peptide was synthetically generated
<221> NAME/KEY: MOD_RES
<222> LOCATION: (2)
<223> OTHER INFORMATION: /product = alpha-aminoisobutryic/label = Aib

<400> SEQUENCE: 6

Cys Xaa Gly Gly
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (4)
<223> OTHER INFORMATION: /product = alpha-aminoisobutryic/label = Aib

<400> SEQUENCE: 7

Cys Ala Gly Xaa
  1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (4)
<223> OTHER INFORMATION: /product = alpha-aminoisobutryic/label = Aib

<400> SEQUENCE: 8

Gly Gly Gly Xaa
  1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (3)
<223> OTHER INFORMATION: /product = alpha-aminoisobutryic/label = Aib

<400> SEQUENCE: 9

Gly Gly Xaa Ala
  1

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (1)
<223> OTHER INFORMATION: /product = diethylene triamine pentaacetic acid
      Amino caprioic acid/label =  DTPA-Acp
<221> NAME/KEY: MOD_RES
<222> LOCATION: (5)
<223> OTHER INFORMATION: /product = alpha-aminoisobutyric acid/label =
      Aib
```

-continued

```
<221> NAME/KEY: MOD_RES
<222> LOCATION: (7)
<223> OTHER INFORMATION: /product = 4-chloro-D-phenylalanine/label =
      4-Cl-D-Phe

<400> SEQUENCE: 10

Xaa His Ser Asp Xaa Val Xaa Thr Asp Asn Tyr Thr Arg Leu Arg Lys
 1               5                  10                  15

Gln Leu Ala Val Lys Lys Tyr Leu Asn Ser Ile Leu Asn
             20                  25

<210> SEQ ID NO 11
<211> LENGTH: 33
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (3)
<223> OTHER INFORMATION: /product = alpha-aminoisobutyric acid/label =
      Aib
<221> NAME/KEY: MOD_RES
<222> LOCATION: (5)
<223> OTHER INFORMATION: /product = Amino caproic acid/label = Acp
<221> NAME/KEY: MOD_RES
<222> LOCATION: (9)
<223> OTHER INFORMATION: /product = alpha-aminoisobutyric acid/label =
      Aib
<221> NAME/KEY: MOD_RES
<222> LOCATION: (11)
<223> OTHER INFORMATION: /product = 4-chloro-D-phenylalanine/label =
      4-Cl-D-Phe

<400> SEQUENCE: 11

Cys Gly Xaa Ala Xaa His Ser Asp Xaa Val Xaa Thr Asp Asn Tyr Thr
 1               5                  10                  15

Arg Leu Arg Lys Gln Leu Ala Val Lys Lys Tyr Leu Asn Ser Ile Leu
             20                  25                  30

Asn

<210> SEQ ID NO 12
<211> LENGTH: 19
<212> TYPE: PRT
<213> ORGANISM: Sus barbatus

<400> SEQUENCE: 12

Tyr Thr Arg Leu Arg Lys Gln Leu Ala Val Lys Lys Tyr Leu Asn Ser
 1               5                  10                  15

Ile Leu Asn
```